(12) United States Patent
Mägerlein et al.

(10) Patent No.: US 8,772,548 B2
(45) Date of Patent: *Jul. 8, 2014

(54) REACTION OF GLYCOLALDEHYDE WITH AN AMINATING AGENT

(75) Inventors: Wolfgang Mägerlein, Mannheim (DE); Johann-Peter Melder, Böhl-Iggelheim (DE); Jörg Pastre, Bensheim (DE); Jan Eberhardt, Mannheim (DE); Thomas Krug, Worms (DE); Mirko Kreitschmann, Mannheim (DE)

(73) Assignee: BASF SE (DE)

( * ) Notice: Subject to any disclaimer, the term of this patent is extended or adjusted under 35 U.S.C. 154(b) by 11 days.

This patent is subject to a terminal disclaimer.

(21) Appl. No.: 13/516,479

(22) PCT Filed: Dec. 14, 2010

(86) PCT No.: PCT/EP2010/069642
§ 371 (c)(1),
(2), (4) Date: Jun. 15, 2012

(87) PCT Pub. No.: WO2011/082994
PCT Pub. Date: Jul. 14, 2011

(65) Prior Publication Data
US 2012/0271068 A1 Oct. 25, 2012

(30) Foreign Application Priority Data
Dec. 17, 2009 (EP) .................... 09179710

(51) Int. Cl.
*C07C 209/26* (2006.01)
*C07C 209/28* (2006.01)
(52) U.S. Cl.
USPC ........................................ 564/473

(58) Field of Classification Search
None
See application file for complete search history.

(56) References Cited

U.S. PATENT DOCUMENTS 6,147,261 A    11/2000   Knifton et al.
6,534,441 B1    3/2003   Bartley et al.

FOREIGN PATENT DOCUMENTS

| DE | 4400591 A1 | 7/1995 | |
| EP | 0663389 * | 7/1995 | ............... B01J 23/46 |
| EP | 0737514 A1 | 10/1996 | |

OTHER PUBLICATIONS

Morrow, Duane F., et al., "Antifertility Activity of Some β-Amino Alcohols", Journal of Medicinal Chemistry, vol. 16, No. 6, (1973), pp. 736-739.
International Search Report for PCT/EP2010/069642 mailed Jun. 6, 2011.
International Preliminary Report on Patentability for PCT/EP2010/069642 mailed Jan. 17, 2012.
Translation of the International Preliminary Report on Patentability for PCT/EP2010/069642 dated Jul. 30, 2012.

* cited by examiner

*Primary Examiner* — Brian J Davis
(74) *Attorney, Agent, or Firm* — Drinker Biddle & Reath LLP

(57) ABSTRACT

The present invention relates to a process for reacting glycolaldehyde with an aminating agent in the presence of hydrogen and of a catalyst, the catalyst being activated by reducing a catalyst precursor or by reducing a passivated catalyst, which comprises effecting the reaction in the presence of a solvent and contacting the glycolaldehyde with the activated catalyst.

9 Claims, No Drawings

US 8,772,548 B2

REACTION OF GLYCOLALDEHYDE WITH AN AMINATING AGENT

CROSS-REFERENCE TO RELATED APPLICATIONS

This application is a national stage application (under 35 U.S.C. §371) of PCT/EP2010/069642, filed Dec. 14, 2010, which claims benefit of European Application No. 09179710.0, filed Dec. 17, 2009, both of which are incorporated herein by reference in their entirety.

The present invention relates to the reaction of glycolaldehyde with an aminating agent.

The reaction of hydroxy-substituted aldehydes with aminating agents, such as ammonia, is known from the prior art.

Houben/Weyl, Methoden der organischen Chemie [Methods of Organic Chemistry], Vol. XI/1, 4$^{th}$ ed., Georg Thieme Verlag Stuttgart, 1957, pages 602 to 648 discloses nickel or cobalt catalysts, in particular in the form of the Raney metals thereof, and catalysts of the Pt group for hydrogenating amination of hydroxy-substituted aldehydes or ketones.

U.S. Pat. No. 4,153,581 relates to the amination of alcohols, aldehydes or ketones by means of specific Co/Cu catalysts which comprise Fe, Zn and/or Zr, while U.S. Pat. No. 4,152,353 relates to the amination of alcohols, aldehydes or ketones by means of specific Ni/Cu catalysts which comprise Fe, Zn and/or Zr.

WO 03/076386 A and EP 1 431 271 A1 describe processes for preparing amines from alcohols, aldehydes or ketones, and nitrogen compounds using a catalyst whose catalytically active material comprises 22-40% by weight (or 22-45% by weight) of oxygen compounds of zirconium, 1-30% by weight of oxygen compounds of copper, and 15-50% by weight (or 5-50% by weight) in each case of oxygen compounds of nickel and of cobalt.

Five patent applications (WO-A-2008/006750, WO-A-2008/006748, WO-A-2008/006752, WO-A-2008/006749, WO-A-2008/006754) relate to particular doped zirconium dioxide-, copper- and nickel-containing catalysts, and to the use thereof in processes for preparing an amine by reacting a primary or secondary alcohol, aldehyde and/or ketone with hydrogen and ammonia, a primary or secondary amine.

The catalysts described in the abovementioned applications comprise 10 to 50% by weight of Co.

DE-A-211 82 83 relates to a process for preparing secondary or tertiary aliphatic or cycloaliphatic amines by reacting an aliphatic or cycloaliphatic carbonyl compound with ammonia using a Pd/Ag fixed bed catalyst. The support material is especially SiO$_2$.

EP-A-2 312 253 describes the use of specific copper catalysts in the preparation of N-substituted amines from alcohols or aldehydes.

DE 3609978 A1 describes a process for preparing hydroxy amines from hydroxy carbonyl compounds, which generically also include glycolaldehyde. In a two-stage process, the carbonyl compound is first reacted with the aminating agent, before the imine obtained is hydrogenated with hydrogen in a second step to give the corresponding amine.

Although the abovementioned references generically encompass the reaction of aldehydes, including hydroxy-substituted aldehydes, the reaction of glycolaldehyde is not explicitly disclosed.

U.S. Pat. No. 6,534,441 describes a process for reductive amination of lower aliphatic alkane derivatives using a nickel/rhenium catalyst. A possible feedstock mentioned in the description is glycolaldehyde. The nickel/rhenium catalyst is prepared by impregnating an aluminosilicate catalyst support with a solution of a nickel salt and of a rhenium salt. This may be followed by a calcination of the catalyst thus obtained. The weight ratio of nickel to rhenium is in the range from 1:1 to 200:1. Before use, the calcined catalyst can be activated or reduced. The alkane derivatives are generally converted in the range from 125 to 350° C., and a pressure of approx. 25 to 350 bar. The reaction is generally performed continuously. The use of a solvent in the reaction is not mentioned.

German patent application DE-A1-4400591 describes a process for preparing amino alcohols by reacting hydroxy carbonyl compounds with hydrogen and an aminating agent at temperatures of 0 to 300° C. and pressures of 1 to 400 bar over a catalyst which comprises 50 to 100% by weight of ruthenium. The reaction can be performed in the absence or presence of an inert solvent. One possible feedstock mentioned is glycolaldehyde. It can likewise be inferred from DE-A1-4400591 that the amination of hydroxy aldehydes leads to colored products. DE-A1-4400591 therefore teaches the use of catalysts which comprise the noble metal ruthenium in high concentration.

The conversion of hydroxy alkanals to diamines in the presence of ammonia and hydrogen in the presence of catalysts which comprise nickel or cobalt is disclosed in U.S. Pat. No. 6,147,261. The hydroxy alkanals can be converted to the corresponding diamines in a one-stage reaction at temperatures of 140 to 180° C. and a pressure of at least 35 bar. 3-Hydroxypropionaldehyde can also be converted in a two-stage reaction, wherein 3-aminopropanol is formed in the first process stage and is converted to propylenediamine in a subsequent second stage. The first stage is effected at temperatures of more than 50° C., preferably of 100 to 150° C., and a pressure of more than 35 bar. The second stage is performed at a temperature of 140 to 200° C. In the first stage, the yield of 3-aminopropanol is not more than 84%. The conversion of hydroxypropanal is essentially quantitative. The conversion can optionally be performed in the presence of a solvent, such as water or higher hydrocarbons. The catalysts are not activated or reduced before use.

U.S. Pat. No. 6,147,261 teaches that hydroxypropionaldehyde is very reactive and tends to oligomerization and polymerization. The reaction of hydroxypropionaldehyde with ammonia is therefore preferably performed in the presence of a solvent.

Although U.S. Pat. No. 6,147,261, DE-A1-4400591 and U.S. Pat. No. 6,534,441 mention the use of glycolaldehyde as a feedstock in a reaction with an aminating agent, the specific reaction demonstrated by examples has not been described.

In contrast to the higher homologs, glycolaldehyde has an even greater tendency to form the dimer, in this case 2,5-dihydroxy-1,4-dioxane, a six-membered ring compound formed preferentially owing to its thermodynamic stability.

For instance, glycolaldehyde in the solid state exists exclusively in dimeric form (A. Beeby, D. B. H. Mohammed, J. R. Sodeau, J. Am. Chem. Soc., 109 (1987), 857-861). In non-aqueous solution, glycolaldehyde is likewise present as the monomer only in small amounts (<6%). The majority is an equilibrium mixture of 5- and 6-membered ring dimers (loc. cit.). In aqueous solution, glycolaldehyde exists mainly in the form of the hydrate (approx. 70%) and in dimeric form (approx. 26%). In the equilibrium mixture, only approx. 4% of the glycolaldehyde is present in monomeric form (loc. cit.). In solution, the aldehyde function to be aminated in the monomeric glycolaldehyde is thus present only in very minor amounts. In addition, in glycolaldehyde as a CH-acidic compound, there is a very high tendency to polymerize in an aldol condensation to form higher sugar alcohols, which forms highly colored products and greatly reduces the yield of target product.

It was therefore an object of the present invention to develop a process for aminating glycolaldehyde, which enables a high conversion of glycolaldehyde and the formation of the products, especially of ethanolamine (MEOA) and ethylenediamine (EDA), in high yield and selectivity. More particularly, the formation of the piperazine by-product should be reduced, since it can be removed from MEOA or EDA only with difficulty and is troublesome in many applications. In addition, the reaction products should be obtained in a high purity. These aims should be achieved under the premise that it is possible to use a catalyst which is very substantially free of noble metals in order to lower the material costs of the process. This is because the use of noble metal catalysts leads to a significant increase in the catalyst use costs, which affect the economic viability of the process. In the future, a severe scarcity of raw materials can be expected, and so it can be expected that the costs of noble metals will rise still further.

Moreover, the catalyst should have a high mechanical and chemical stability in order to ensure long service lives.

It was a further object of the present invention to minimize leaching of metals, for example aluminum in the case of skeletal catalysts or alkaline promoters such as lithium, out of the catalyst, since this leads to declining stability and deactivation of the catalyst. Aluminates which form under basic conditions from the leached aluminum can, as solid residues, lead to blockages and deposits, and cause the decomposition of product of value.

The object is achieved by a process for reacting glycolaldehyde with an aminating agent in the presence of hydrogen and of a catalyst, the catalyst being activated by reducing a catalyst precursor or by reducing a passivated catalyst, which comprises effecting the reaction in the presence of a solvent and contacting the glycolaldehyde with the activated catalyst.

In the process according to the invention, glycolaldehyde is used. Glycolaldehyde is commercially available and can be prepared, for example, by oxidizing ethylene glycol (see, for example, JP 3246248 and JP 3279342). Glycolaldehyde is preferably synthesized by reaction of formaldehyde with carbon monoxide and hydrogen, as described, for example, in US 2009012333, US 2008081931, US 2007249871, EP 1697291, U.S. Pat. No. 4,503,260 and U.S. Pat. No. 4,322,568.

A further starting material used in the process according to the invention is an aminating agent.

The aminating agents used in the hydrogenating amination of alcohols, aldehydes or ketones in the presence of hydrogen may be either ammonia or primary or secondary aliphatic or cycloaliphatic or aromatic amines.

The aminating agent is preferably a nitrogen compound of the formula I

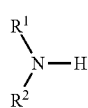

(I)

in which
$R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $C_{3-30}$-dialkylaminoalkyl, aryl, aralkyl such as $C_{7-20}$-aralkyl, and alkylaryl such as $C_{7-20}$-alkylaryl, or together are —$(CH_2)_j$—X—$(CH_2)_k$—,
X is $CH_2$, $CHR^3$, oxygen (O), sulfur (S) or $NR^3$,
$R^3$ is hydrogen (H), alkyl such as $C_{1-4}$-alkyl, alkylphenyl such as $C_{7-40}$-alkylphenyl,
j, k are each integers from 1 to 4.

Particular preference is given to using ammonia and the following mono- and dialkylamines as aminating agents: monomethylamine, dimethylamine, monoethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine. Especially preferred aminating agents are ammonia, and monomethylamine and dimethylamine. Very particular preference is given to using ammonia as the aminating agent.

A further feedstock used in the process according to the invention is hydrogen. The hydrogen is generally used in technical grade purity. The hydrogen can also be used in the form of a hydrogen-comprising gas, i.e. in mixtures with other inert gases, such as nitrogen, helium, neon, argon or carbon dioxide. The hydrogen-comprising gases used may, for example, be reformer offgases, refinery gases, etc., provided that these gases do not comprise any catalyst poisons for the catalysts used, for example CO. Preference is given, however, to using pure hydrogen or essentially pure hydrogen in the process, for example hydrogen with a content of more than 99% by weight of hydrogen, preferably more than 99.9% by weight of hydrogen, more preferably more than 99.99% by weight of hydrogen, especially more than 99.999% by weight of hydrogen.

According to the invention, the reaction of glycolaldehyde with an aminating agent in the presence of hydrogen takes place in a solvent.

The solvent used may be any solvent which is inert under the reaction conditions and has a sufficient solubility for the reactants and reaction products.

Preferred solvents are water; ethers such as methyl tert-butyl ether, ethyl tert-butyl ether, dioxane or tetrahydrofuran (THF).

Useful solvents also include suitable mixtures of the solvents listed above.

Particularly preferred solvents are THF and water.

Particularly preferred solvents also include the reaction products of the inventive reaction of glycolaldehyde and the aminating agent.

The process according to the invention takes place in the presence of a catalyst.

The catalysts may in principle comprise nickel, cobalt, iron, copper, chromium, manganese, copper, molybdenum, tungsten and/or other metals of groups 8 and/or 9 and/or 10 and/or 11 of the periodic table of the elements (Periodic table in the IUPAC version dated Jun. 22, 2007).

Preference is given to using catalysts which comprise copper, cobalt and/or nickel.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

In a preferred embodiment, the catalysts comprise less than 25 mole percent, preferably less than 10 mole percent, more preferably less than 1 mole percent, especially preferably less than 0.4 mole percent and most preferably less than 0.1 mole percent of noble metal atoms, based on the total number of metal atoms in the catalyst. The term "noble metals" refers in the context of the present invention to metals selected from the group consisting of ruthenium, rhodium, palladium, silver, rhenium, osmium, iridium, platinum, gold and mercury.

The number of metal atoms present in the catalyst can be measured by means of known elemental analysis methods, for example atomic absorption spectrometry (AAS), atomic emission spectrometry (AES), x-ray fluorescence analysis (XFA) or ICP-OES (Inductively Coupled Plasma Optical Emission Spectrometry).

In the process according to the invention, catalysts which are prepared by reduction of catalyst precursors are used.

The catalyst precursor comprises an active material which comprises one or more catalytically active components and optionally a support material.

The catalytically active components are oxygen compounds of the abovementioned metals, for example the metal oxides or hydroxides thereof, such as CoO, NiO, CuO and/or mixed oxides thereof.

In the context of this application, the term "catalytically active components" is used for abovementioned oxygen-metal compounds, but is not intended to imply that these oxygen compounds are already catalytically active per se. The catalytically active components generally have catalytic activity in the inventive conversion only on completion of reduction.

The catalyst precursors can be prepared by known processes, for example by precipitation, precipitative application or impregnation.

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying.

Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or the doping elements, such as cobalt nitrate or cobalt chloride.

Thereafter, the impregnated support material is generally dried and optionally calcined. The impregnation can also be effected by the so-called "incipient wetness method", in which the support material is moistened with the impregnating solution up to a maximum of saturation according to its water absorption capacity. However, the impregnation can also be effected in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be effected simultaneously with all metal salts or in any desired sequence of the individual metal salts.

In a further preferred embodiment, catalyst precursors are prepared by means of a coprecipitation of all of their components. To this end, in general, a soluble compound of the corresponding active component and of the doping elements, and optionally a soluble compound of a support material are admixed with a precipitant in a liquid while heating and while stirring until the precipitation is complete.

The liquid used is generally water.

Useful soluble compounds of the active components typically include the corresponding metal salts, such as the nitrates, sulfates, acetates or chlorides of the aforementioned metals.

The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides, are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates formed in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be effected, for example, by adjusting the precipitation catalyst to a particular particle size by grinding.

After the grinding, the catalyst precursor obtained by precipitation reactions can be mixed with shaping assistants such as graphite or stearic acid, and processed further to shaped bodies.

Common processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granules, spheres, cylinders or grains. Common processes for shaping are, for example, extrusion, tableting, i.e. mechanical pressing, or pelletizing, i.e. compacting by circular and/or rotating motions. The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as the oxides, mixed oxides and/or hydroxides. The catalyst precursors thus prepared can be stored as such.

Particular preference is given to catalyst precursors such as the oxide mixtures which are disclosed in EP-A-0636409 and which comprise, before the reduction with hydrogen, 55 to 98% by weight of Co, calculated as CoO, 0.2 to 15% by weight of phosphorus, calculated as $H_3PO_4$, 0.2 to 15% by weight of manganese, calculated as $MnO_2$, and 0.2 to 5.0% by weight of alkali metal, calculated as $M_2O$ (M=alkali metal), or oxide mixtures which are disclosed in EP-A-0742045 and which comprise, before the reduction with hydrogen, 55 to 98% by weight of Co, calculated as CoO, 0.2 to 15% by weight of phosphorus, calculated as $H_3PO_4$, 0.2 to 15% by weight of manganese, calculated as $MnO_2$, and 0.05 to 5% by weight of alkali metal, calculated as $M_2O$ (M=alkali metal), or oxide mixtures which are disclosed in EP-A-696572 and which comprise, before the reduction with hydrogen, 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or manganese, calculated as $Al_2O_3$ and $MnO_2$ respectively, for example the catalyst disclosed in loc. cit., page 8, with the composition of 31.5% by weight of $ZrO_2$, 50% by weight of NiO, 17% by weight of CuO and 1.5% by weight of $MoO_3$, or oxide mixtures which are disclosed in EP-A-963 975 and which comprise, before the reduction with hydrogen, 22 to 40% by weight of $ZrO_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or manganese, calculated as $Al_3O_3$ and $MnO_2$ respectively, and no oxygen compounds of molybdenum, for example the catalyst A disclosed in loc. cit., page 17, with the composition of 33% by weight of Zr, calculated as $ZrO_2$, 28% by weight of Ni, calculated as NiO, 11% by weight of Cu, calculated as CuO and 28% by weight of Co, calculated as CoO.

The catalyst which is used in the process according to the invention is obtained by reducing catalyst precursors which have been prepared by impregnation or precipitation as described above after the calcination or conditioning.

The reduction of the dry, generally pulverulent catalyst precursor can be performed at elevated temperature in a moving or stationary reduction oven.

The reducing agent used is typically hydrogen or a hydrogen-comprising gas.

The hydrogen is generally used in technical grade purity. The hydrogen can also be used in the form of a hydrogen-comprising gas, i.e. in admixtures with other inert gases, such as nitrogen, helium, neon, argon or carbon dioxide. The hydrogen stream can also be recycled into the reduction as cycle gas, optionally mixed with fresh hydrogen and optionally after removing water by condensation.

The catalyst precursor is preferably reduced in a reactor in which the shaped catalyst bodies are arranged as a fixed bed. The catalyst precursor is more preferably reduced in the same reactor in which the subsequent reaction of glycolaldehyde with aminating agent is effected.

In addition, the catalyst precursor can be reduced in a fluidized bed reactor in the fluidized bed.

The catalyst precursor is generally reduced at reduction temperatures of 50 to 600° C., especially of 100 to 500° C., more preferably of 150 to 450° C.

The partial hydrogen pressure is generally from 1 to 300 bar, especially from 1 to 200 bar, more preferably from 1 to 100 bar, where the pressure figures here and hereinafter are based on the absolute measured pressure.

The duration of the reduction is preferably 1 to 20 hours and more preferably 5 to 15 hours.

During the reduction, a solvent can be supplied in order to remove water of reaction which forms and/or in order, for example, to be able to heat the reactor more rapidly and/or to be able to better remove the heat during the reduction. In this case, the solvent can also be supplied in supercritical form.

Suitable solvents used may be the above-described solvents. Preferred solvents are water; ethers such as methyl tert-butyl ether, ethyl tert-butyl ether, dioxane or tetrahydrofuran. Particular preference is given to water or tetrahydrofuran. Suitable solvents likewise include suitable mixtures.

The catalyst precursor can also be reduced in suspension, for example in a stirred autoclave. The temperatures are generally within a range from 50 to 300° C., especially from 100 to 250° C., more preferably from 120 to 200° C.

The reduction in suspension is generally performed at a partial hydrogen pressure of 1 to 300 bar, preferably from 10 to 250 bar, more preferably from 30 to 200 bar. Useful solvents include the aforementioned solvents.

The duration of the reduction in suspension is preferably 5 to 20 hours, more preferably 8 to 15 hours.

The catalyst can be handled under inert conditions after the reduction. The catalyst can preferably be handled and stored under an inert gas such as nitrogen, or under an inert liquid, for example an alcohol, water or the product of the particular reaction for which the catalyst is used. If appropriate, the catalyst must then be freed of the inert liquid before commencement of the actual reaction.

The storage of the catalyst under inert substances enables uncomplicated and safe handling and storage of the catalyst.

After the reduction, the catalyst can also be contacted with an oxygen-comprising gas stream such as air or a mixture of air with nitrogen. This affords a passivated catalyst. The passivated catalyst generally has a protective oxide layer. This protective oxide layer simplifies the handling and storage of the catalyst, such that, for example, the installation of the passivated catalyst into the reactor is simplified.

According to the invention, glycolaldehyde is contacted with an activated catalyst.

According to the invention, a catalyst is activated by reducing a catalyst precursor or by reducing a passivated catalyst.

In the context of the present invention, an activated catalyst is a catalyst which has been prepared by reducing a catalyst precursor and which has been handled under inert conditions during and after the reduction until the contacting with glycolaldehyde. In the context of the present invention, an activated catalyst is also a catalyst which has been prepared by reduction of a passivated catalyst and which has been handled under inert conditions during and after the reduction until the contacting with glycolaldehyde.

In such a catalyst, the metals are present partly in reduced form, and such a catalyst generally does not have a protective oxide layer.

A measure of the activation of a catalyst is the degree of reduction.

In a preferred embodiment, the degree of reduction of the activated catalyst is 30% or more, preferably 50% or more, more preferably 75% or more and especially preferably 90% or more.

In a preferred embodiment, an activated catalyst which has been prepared by reducing a passivated catalyst has, after the activation, a degree of reduction which is at least 2%, preferably at least 3% and more preferably at least 4% above the degree of reduction of the passivated catalyst.

The degree of reduction is generally determined by "temperature-programmed reduction" (TPR).

Temperature-programmed reduction is effected by heating the sample of the catalyst precursor in a hydrogen/inert gas stream with a constant temperature increase per unit time. Preference is given to using an arrangement whose construction is based on the proposals by Monti and Baiker [D. A. M. Monti, A. Baiker, "Temperature-Programmed Reduction. Parametric Sensitivity and Estimation of Kinetic Parameters", J. Catal. 83 (1983) 323-335].

In this test setup, the pulverulent samples are introduced into a U-shaped glass tube as a loose bed between two glass wool plugs. The U-tube is within a ceramic tube oven. After installation into the TPR apparatus, the sample is first dried by heating it to 200° C. in an argon stream and holding it there for 30 minutes. Subsequently, it is cooled to 50° C. The sample is heated with a heating ramp of 5 K/min from 50° C. to an end temperature of 650° C. The sample temperature is measured in a thermocouple sleeve close to the bed and recorded at intervals of 2 s. A hydrogen/argon stream with 10% hydrogen is passed through the U-tube. The hydrogen content in the offgas is determined with a thermal conductivity detector. The hydrogen consumption is recorded as a function of temperature. By integration, the total $H_2$ consumption within the temperature range of interest is determined.

The degree of reduction RG can be calculated from the $H_2$ consumption by the following formula:

RG=100%−100%*[(measured hydrogen consumption of the catalyst sample (from TPR measurement))/ (theoretical hydrogen consumption of the fully oxidic catalyst which is calculated on the basis of the metal contents of the sample and reaction stoichiometry)]

In the calculation of the theoretical hydrogen consumption, the assumption is made that Ni, Cu and Co are present as NiO, CuO and CoO, and the aforementioned promoters are not present in reduced form. This is because, in the calculation of the degree of reduction, typically only those metal oxides which are reduced to the corresponding metals under the conditions of the TPR measurement are considered. For example, $ZrO_2$ is not reduced under the conditions of the TPR measurement, and so the Zr content is not taken into account in the determination of the degree of reduction.

The catalyst is activated by reducing a catalyst precursor. The reduction of a catalyst precursor has already been described above.

A catalyst can also be activated by reducing a passivated catalyst. A passivated catalyst can be reduced as described above by treating the passivated catalyst with hydrogen or a hydrogen-comprising gas. The reduction conditions correspond generally to the reduction conditions employed in the reduction of the catalyst precursors. The activation generally eliminates the protective passivation layer.

An activated catalyst has to be handled under inert conditions during and after the activating reduction thereof.

The activated catalyst is preferably handled and stored under an inert gas, such as nitrogen, or under an inert liquid, for example an alcohol, water or the product of the particular reaction for which the catalyst is used. If appropriate, the activated catalyst then has to be freed of the inert liquid before commencement of the actual reaction.

According to the invention, the glycolaldehyde is contacted with the activated catalyst. According to the invention, the activated catalyst is handled under inert conditions during and after the activation until the contacting. The glycolaldehyde is preferably also contacted with the activated catalyst under inert conditions, more preferably in the presence of hydrogen or a hydrogen-comprising gas.

In a preferred embodiment, the activated catalyst is contacted with glycolaldehyde in the reactor in which the catalyst has already been activated beforehand. According to the invention, the activated catalyst is handled under inert conditions during and after the activation until the contacting, preferably in the presence of hydrogen or a hydrogen-comprising gas. Alternatively, the activated catalyst, after it has been activated, can be stored in the presence of nitrogen or another suitable inert gas. To this end, the proportion of the inert gas in the hydrogen stream is generally increased gradually after the activation. Preference is also given to metering in the glycolaldehyde under inert conditions, preferably in the presence of hydrogen or of an inert gas. In a further preferred embodiment, the activated catalyst is contacted with an inert liquid after the activation.

The activated catalyst is preferably contacted with an inert liquid by metering the inert liquid into the activated catalyst. The inventive conversion of glycolaldehyde preferably takes place in the same reactor in which the activation of the catalyst has also been undertaken.

The catalyst can, however, also be transferred together with the inert liquid into the reactor in which the contacting with glycolaldehyde is effected. The glycolaldehyde may already be present as an initial charge in the reactor, but it can also be metered into the reactor after the transfer of the catalyst. The contacting of the activated catalyst with glycolaldehyde preferably takes place under inert conditions, more preferably in the presence of hydrogen or of an inert gas.

In the process according to the invention, glycolaldehyde is reacted with an aminating agent in the presence of hydrogen and a solvent.

The solvent can be used in a proportion of 5 to 95% by weight, preferably 20 to 70%, more preferably 30 to 60%, based in each case on the total weight of the reaction mixture, where the total weight of the reaction mixture is composed of the sum of the masses of the starting materials (glycolaldehyde and aminating agent) and solvents used in the process.

The ratio of aminating agent to the glycolaldehyde used is typically within a range from 1:100 to 100:1, preferably 1:1 to 50:1 and more preferably 1:1 to 45:1.

The reaction is typically performed at a pressure of 1 to 500 bar, preferably 10 to 350 bar, more preferably at a pressure of 50 to 300 bar and most preferably 80 to 220 bar. The pressure is maintained or controlled generally via the metered addition of the hydrogen.

The reaction of glycolaldehyde with aminating agent generally proceeds at temperatures of 15 to 350° C., preferably 50 to 250° C., more preferably 80 to 220° C.

In a particularly preferred embodiment, the ratio of aminating agent to glycolaldehyde used is preferably 1:100 to 100:1, more preferably 1:1 to 50:1 and most preferably 1:1 to 45:1. In this particularly preferred embodiment, the pressure is preferably 1 to 200 bar, more preferably 10 to 150 bar and most preferably 50 to 120 bar, and the temperature is preferably 20 to 300° C., more preferably 50 to 250° C. and most preferably 80 to 120° C. In this particular embodiment, the conversion of glycolaldehyde generally forms MEOA with high selectivity and yield.

In a further particularly preferred embodiment, the ratio of aminating agent to glycolaldehyde used is preferably 1:100 to 100:1, more preferably 1:1 to 50:1 and most preferably 1:1 to 45:1. In this particularly preferred embodiment, the pressure is preferably 100 to 300 bar, more preferably 150 to 250 bar and most preferably 180 to 220 bar, and the temperature is preferably 20 to 300° C., more preferably 50 to 250° C. and very particularly 160 to 220° C. In this particular embodiment, the conversion of glycolaldehyde generally forms EDA with high selectivity and yield.

The process according to the invention can be performed continuously, batchwise or semicontinuously.

Typical reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and removal/supply of substreams between the trays, in possible embodiments as radial flow or axial flow reactors, continuous stirred tanks, bubble reactors, etc., the reactor used in each case being that suitable for the desired reaction conditions (such as temperature, pressure and residence time).

The process according to the invention is preferably performed in a high-pressure stirred tank reactor, fixed bed reactor or fluidized bed reactor.

In a particularly preferred embodiment, the process according to the invention is performed in one or more fixed bed reactors.

In a further particularly preferred embodiment, glycolaldehyde is converted in a high-pressure stirred tank reactor.

The glycolaldehyde and the aminating agent can be added together to the reaction zone of the reactor, for example as a premixed reactant stream, or separately. In the case of separate addition, the glycolaldehyde and the aminating agent can be added to the reaction zone of the reactor simultaneously, offset in time or successively.

The residence time in the process according to the invention, in the case of performance in a batchwise process, is generally 15 minutes to 72 hours, preferably 60 minutes to 24 hours, more preferably 2 hours to 10 hours.

In the case of performance in a preferred continuous process, the catalyst hourly space velocity is generally in the range from 0.01 kg of glycolaldehyde/kg of catalyst/h to 3.0 kg of glycolaldehyde/kg of catalyst/h, preferably 0.05 kg of glycolaldehyde/kg of catalyst/h to 2.0 kg of glycolaldehyde/kg of catalyst/h and more preferably 0.1 kg of glycolaldehyde/kg of catalyst/h–1.5 kg of glycolaldehyde/kg of catalyst/h.

After the inventive reaction, the desired product can be isolated by processes known to those skilled in the art, for example by distillation.

The advantages of the present invention are that it has been possible to develop a process for converting glycolaldehyde which enables a high conversion of glycolaldehyde and the formation of products, especially of MEOA and/or EDA, in high yield and selectivity. In addition, the formation of the undesired piperazine by-product is reduced. Moreover, the conversion products are obtained in a high purity. These aims have been achieved under the premise that it is possible to use catalysts which are very substantially free of noble metals in the process according to the invention. The material costs of the process can therefore be lowered. This is because the use of noble metal catalysts leads to a great increase in the catalyst use costs, which has an adverse effect on the economic viability of the process. In the future, severe scarcity of raw materials can be anticipated, and so it can be expected that the prices of noble metals will rise further.

Furthermore, the catalysts in the process according to the invention have a high mechanical and chemical stability, and so long service lives can be achieved.

The process according to the invention is illustrated in detail with reference to the examples adduced below.

Preparation of the Catalyst Precursors

Catalyst Precursor a)

An aqueous solution of nickel nitrate, copper nitrate and zirconium acetate, which comprises 4.48% by weight of Ni (calculated as NiO), 1.52% by weight of Cu (calculated as CuO) and 2.82% by weight of Zr (calculated as $ZrO_2$), is coprecipitated in a stirred vessel in a constant stream with a 20% aqueous sodium carbonate solution at a temperature of 70° C., in such a way that the pH of 7.0 measured with a glass electrode is maintained. The resulting suspension is filtered and the filtercake is washed with demineralized water until the electrical conductivity of the filtrate is approx. 20 µS. Then a sufficient amount of ammonium heptamolybdate is incorporated into the still-moist filtercake that the oxide mixture specified below is obtained. Thereafter, the filtercake is dried at a temperature of 150° C. in a drying cabinet or a spray drier. The hydroxide-carbonate mixture obtained in this way is then heat treated at a temperature of 430 to 460° C. over a period of 4 hours. The catalyst precursor thus prepared has the composition of: 50% by weight of NiO, 17% by weight of CuO, 1.5% by weight of $MoO_3$ and 31.5% by weight of $ZrO_2$. The catalyst was mixed with 3% by weight of graphite and shaped to tablets.

Preparation of Catalyst Precursor (b):

An aqueous solution of nickel nitrate, cobalt nitrate, copper nitrate and zirconium acetate, which comprised 2.39% by weight of NiO, 2.39% by weight of CoO, 0.94% by weight of CuO and 2.82% by weight of $ZrO_2$, was coprecipitated in a stirred vessel in a constant stream with a 20% aqueous sodium carbonate solution at a temperature of 70° C., in such a way that the pH of 7.0 measured with a glass electrode was maintained. The resulting suspension was filtered and the filtercake was washed with demineralized water until the electrical conductivity of the filtrate was approx. 20 µS. Thereafter, the filtercake was dried at a temperature of 150° C. in a drying cabinet or a spray drier. The hydroxide-carbonate mixture obtained in this way was then heat treated at a temperature of 450 to 500° C. over a period of 4 hours. The catalyst precursor thus prepared had the composition of: 28% by weight of NiO, 28% by weight of CoO, 11% by weight of CuO and 33% by weight of $ZrO_2$. The catalyst precursor was mixed with 3% by weight of graphite and shaped to tablets.

Preparation of Catalyst Precursor (c):

By dissolving cobalt nitrate, manganese nitrate and phosphoric acid in water, a solution which comprises 10% by weight of cobalt, 0.55% by weight of manganese and 0.45% by weight of $H_3PO_4$ was prepared. By adding a 20% sodium carbonate solution, precipitation was effected at a temperature of 50° C. The precipitate formed was washed until no sodium or nitrate was detectable any longer in the washing water. The solid thus obtained was slurried with water and sprayed in a spray tower (inlet temperature=550° C.). The sprayed material was dried at 500° C., ground in a pan mill and shaped in an extruder to extrudates of diameter 4 mm. The extrudates were dried at 100 to 120° C. and then calcined at 650° C. for 1 h and then at 850° C. for 3 h. The catalyst precursor thus obtained comprised 90.4% by weight of cobalt, 5.1% by weight of manganese, 0.3% by weight of sodium and 3.1% by weight of phosphorus.

Preparation of Catalyst Precursor (d):

The catalyst precursor (d) was prepared according to Example 1A of EP-A-1317959, except without using iron (III) chloride.

Preparation of Catalyst (e):

The catalyst (e) used was commercially available Ni-1404 from Engelhardt (Engelhardt Co., Iselin, N.J.). This catalyst consists of Ni and NiO, and also aluminum oxides and silicon oxides. The catalyst was already supplied by the manufacturer in reduced and passivated form and was used in pulverulent form.

Reduction and Passivation of the Catalyst Precursors

The oxidic tablets (catalyst precursors (a) and (b)) or extrudates (catalyst precursor (c)) or powder (catalyst precursor (d)) were reduced.

According to the catalyst precursor, the reduction was performed in the range from 250 to 500° C. at a heating rate of 3° C./minute. Reduction was effected first with 10% $H_2$ in $N_2$ for 50 minutes, then with 25% $H_2$ in $N_2$ for 20 minutes, then with 50% $H_2$ in $N_2$ for 10 minutes, then with 75% $H_2$ in $N_2$ for 10 minutes and finally with 100% $H_2$ for 3 hours. The percentages are each percentages by volume. The passivation of the reduced catalysts was performed at room temperature in dilute air (air in $N_2$ with an $O_2$ content of not more than 5% by volume).

Conversions of Glycolaldehyde

Examples 1 to 12

An electrically heated 160 ml autoclave (Hastelloy) with a mechanical magnet-coupled stirrer was initially charged with 3 g of commercial dimeric glycolaldehyde (50 mmol, calculated as the monomer) in the particular solvent (20 ml). Subsequently, the amount of the activated catalyst specified in Table 1 was added under an inert gas atmosphere, suspended in 10 ml of THF.

Before introduction into the autoclave, the passivated catalyst was activated as follows:

In Examples 1 to 3, the passivated catalyst was reduced at 280° C. at a partial hydrogen pressure of 1 bar for 10 hours.

The degree of reduction was more than 30% in all cases.

In Examples 4 to 11, the passivated catalyst was reduced at 280° C. at a partial hydrogen pressure of 1 bar for 10 hours.

The degree of reduction was more than 30% in all cases.

In Example 12, the passivated catalyst was not activated (comparative example).

Subsequently, ammonia, according to the molar ratio specified in Table 1 (ammonia:monomeric glycolaldehyde), was metered in and the mixture was heated to 100° C. On attainment of this temperature, a sufficient amount of hydrogen was injected that the reaction pressure specified was attained. During the reaction, the pressure was maintained by supplying further hydrogen, and the consumption was measured. In all cases, stirring was effected at 100° C. and the particular pressure for 8 h. The conversion was determined approximately with the aid of the hydrogen consumption.

The reaction output was filtered off from the catalyst after 8 h, admixed with methanol and analyzed by GC (area percent).

The difference from 100% is unidentified secondary components.

Examples 13 to 16

An electrically heated 160 ml autoclave (Hastelloy) with a mechanical magnet-coupled stirrer was initially charged with 3 g of commercial dimeric glycolaldehyde (50 mmol, calculated as the monomer) in 20 ml of THF. 500 µl (0.47 g) of diethylene glycol dimethyl ether were added as an internal standard. Subsequently, 0.5 g of catalyst suspended in 10 ml of THF was added under an inert gas atmosphere.

In the case of Examples 14 and 16, the passivated catalyst, in each case before the addition to the reactor, was activated with hydrogen at 250° C. at a partial hydrogen pressure of 1 bar for 10 hours.

The degree of reduction is reported in Table 2.

In Examples 13 and 15, the passivated catalyst was not activated before the addition to the reactor.

Subsequently, 30 g of ammonia, corresponding to a molar ratio (ammonia:monomeric glycolaldehyde) of 35:1, were metered in and the mixture was heated to 100° C. On attainment of this temperature, a sufficient amount of hydrogen was injected that a reaction pressure of 80 bar was attained. During the reaction, the pressure was maintained by supplying further hydrogen and the consumption was measured. The reaction was stirred at 100° C. and 800 rpm. The reaction time is specified in Table 2. The reaction output was filtered off from the catalyst, admixed with methanol and analyzed by GC (area percent). In addition, with the aid of the internal standard, the yield of the compounds listed was determined (Table 2).

Determination of the Degree of Reduction:

The measurement was recorded on a Micromeritics RS 232, Autochem II chemisorption analyzer. The evaluation software used was the program Autochem II 2920.

The temperature-programmed reduction was effected by heating the sample of the catalyst precursor in a hydrogen/inert gas stream with a constant temperature increase per unit time. A setup whose construction is based on the proposals by Monti and Baiker [D. A. M. Monti, A. Baiker, "Temperature-Programmed Reduction. Parametric Sensitivity and Estimation of Kinetic Parameters", J. Catal. 83 (1983) 323-335] was used. The pulverulent samples were introduced into a U-shaped glass tube as a loose bed between two glass wool plugs. The U-tube is within a ceramic tube oven. After installation into the TPR apparatus, the sample was first dried by heating it to 200° C. in an argon stream and holding it there for 30 minutes. Subsequently, it was cooled to 50° C. The sample was heated with a heating ramp of 5 K/min from 50° C. to an end temperature of 650° C. The sample temperature was measured in a thermocouple sleeve close to the bed and recorded at intervals of 2 s. A hydrogen/argon stream with 10% hydrogen was passed through the U-tube. The hydrogen content in the offgas was determined with a thermal conductivity detector. The hydrogen consumption was recorded as a function of temperature. By integration, the total $H_2$ consumption within the temperature range of interest was determined.

The degree of reduction RG was calculated from the $H_2$ consumption by the following formula:

RG=100%−100%*[(measured hydrogen consumption of the catalyst sample (from TPR measurement))/(theoretical hydrogen consumption of the fully oxidic catalyst which is calculated on the basis of the metal contents of the sample and reaction stoichiometry)]

colaldehyde with the activated catalyst, wherein the catalyst precursor comprises, as catalytically active components, one or more oxygen compound of Ni, Co and/or Cu.

2. The process according to claim 1, wherein the catalyst used comprises less than 0.4 mole percent of noble metal atoms selected from the group consisting of ruthenium, rhodium, palladium, silver, rhenium, osmium, iridium, platinum, gold and mercury.

3. The process according to claim 1, wherein the reaction is performed at a temperature of 15 to 350° C.

4. The process according to claim 1, wherein the reaction is performed at a pressure of 10 to 350 bar.

5. The process according to claim 1, wherein the solvent is THF or water.

6. The process according to claim 1, wherein the activated catalyst has a degree of reduction of 30% or more.

7. The process according to claim 1, wherein the activated catalyst which has been prepared by reducing a passivated catalyst has, after the activation, a degree of reduction which is at least 2% greater than the degree of reduction of the passivated catalyst.

8. The process according to claim 1, wherein the activated catalyst is handled under inert conditions during and after the reduction until the contacting with glycolaldehyde.

9. A process for reacting glycolaldehyde with an aminating agent in the presence of hydrogen and of a catalyst, the catalyst being activated by reducing a catalyst precursor or by

TABLE 1

Amination of glycolaldehyde with $NH_3$ to give MEOA.

| Example | Catalyst precursor used | Amount of cat. [g] | Solvent | Temperature [° C.] | Pressure [bar] | Molar ratio of NH3:GA (monomeric) | Conversion [%] | EDA [%] | MEOA [%] | Piperazine [%] | AEEA [%] | DEOA [%] | TEOA [%] |
|---|---|---|---|---|---|---|---|---|---|---|---|---|---|
| 1 | (a) | 0.5 | THF | 100 | 100 | 35 | 100 | 17.2 | 68.7 | 2.3 | 4.6 | 0.0 | 0.0 |
| 2 | (a) | 0.5 | THF | 100 | 100 | 50 | 100 | 13.5 | 76.7 | 1.1 | 3.2 | 0.3 | 0.0 |
| 3 | (b) | 0.5 | THF | 100 | 100 | 35 | 100 | 6.0 | 60.7 | 0.6 | 0.0 | 1.5 | 0.0 |
| 4 | (c) | 0.5 | THF | 100 | 100 | 35 | 100 | 12.7 | 76.5 | 1.3 | 3.4 | 0.3 | 0.0 |
| 5 | (c) | 0.5 | THF | 100 | 60 | 35 | 90 | 12.63 | 67.4 | 2.1 | 3.2 | 1.3 | 0.0 |
| 6 | (c) | 0.5 | THF | 100 | 80 | 35 | 100 | 6.35 | 82.6 | 0.6 | 2.3 | 1.9 | 0.4 |
| 7 | (c) | 0.5 | THF | 100 | 100 | 35 | 100 | 5.77 | 75.1 | 0.5 | 2.2 | 2.5 | 0.4 |
| 8 | (c) | 0.5 | THF | 100 | 100 | 10 | 90 | 5.43 | 68.6 | 0.8 | 3.1 | 9.5 | 0.4 |
| 9 | (c) | 0.5 | THF | 100 | 40 | 10 | 100 | 12.33 | 61.6 | 3.2 | 4.3 | 9.5 | 0.0 |
| 10 | (c) | 0.5 | THF | 100 | 100 | 60 | 100 | 6.83 | 73.5 | 0.6 | 1.5 | 3.8 | 0.0 |
| 11 | (c) | 0.5 | water | 100 | 100 | 35 | >80 | 0.4 | 71.3 | n.d. | n.d. | 1.5 | 0.0 |
| 12 | (d) | 0.23 | THF | 100 | 100 | 35 | 60 | 23.20 | 59.7 | 7.5 | 2.6 | 0.0 | 0.0 |

TABLE 2

Amination of glycolaldehyde with $NH_3$ over reduced/passivated catalysts and over activated catalysts

| Example | Catalyst precursor used | Catalyst pretreatment | Degree of reduction after TPR [%] | Reaction time [h] | EDA [%] | MEOA [%] | Piperazine [%] | AEEA [%] | DEOA [%] | TEOA [%] | EDA yield [%] | MEOA yield [%] | Piperazine yield [%] |
|---|---|---|---|---|---|---|---|---|---|---|---|---|---|
| 13 | (a) | none | 24 | 5.1 | 20.6 | 56.9 | 3.98 | 4.64 | 0.34 | 0.0 | 14.23 | 44.37 | 1.36 |
| 14 | (a) | activation with H2 | 50 | 1.2 | 7.8 | 82.1 | 0.60 | 2.71 | 0.68 | 0.0 | 6.13 | 72.74 | 0.23 |
| 15 | (e) | none | 51 | 2.4 | 14.2 | 60.0 | 2.90 | 3.78 | 0.57 | 0.0 | 7.27 | 34.04 | 0.13 |
| 16 | (e) | activation with H2 | 55 | 1.2 | 4.6 | 85.2 | 0.32 | 1.83 | 2.01 | 0.0 | 3.46 | 72.51 | 0.12 |

The invention claimed is:

1. A process for reacting glycolaldehyde with an aminating agent in the presence of hydrogen and of a catalyst, the catalyst being activated by reducing a catalyst precursor or by reducing a passivated catalyst, which comprises effecting the reaction in the presence of a solvent and contacting the glycolaldehyde with the activated catalyst, wherein the catalyst precursor comprises, as catalytically active components, one or more oxygen compounds of the metals of groups 8 and/or 9 and/or 10 and/or 11 of the periodic table of the elements, and wherein the catalyst used comprises less than 0.4 mole percent of noble metal atoms selected from the group consisting of ruthenium, rhodium, palladium, silver, rhenium, osmium, iridium, platinum, gold and mercury.

* * * * *